United States Patent [19]

Huebel

[11] Patent Number: 4,519,824
[45] Date of Patent: May 28, 1985

[54] HYDROCARBON GAS SEPARATION

[75] Inventor: Robert R. Huebel, Houston, Tex.

[73] Assignee: The Randall Corporation, Houston, Tex.

[21] Appl. No.: 549,044

[22] Filed: Nov. 7, 1983

[51] Int. Cl.$^3$ .............................................. F25J 3/02
[52] U.S. Cl. ........................................ 62/26; 62/28; 62/30; 62/31; 62/33; 62/34; 62/39
[58] Field of Search ............... 62/9, 11, 23, 24, 27, 62/28, 29, 30, 31, 32, 33, 34, 38, 39, 26, 25

[56] References Cited

U.S. PATENT DOCUMENTS 4,061,481 12/1977 Campbell et al. ................... 62/38
4,203,741 5/1980 Bellinger et al. ................... 62/38

*Primary Examiner*—Frank Sever
*Attorney, Agent, or Firm*—Richard H. Berneike

[57] ABSTRACT

A cryogenic process for separating methane from ethane and heavier hydrocarbons in which a high pressure gas feed is divided into two gas streams. The gas is cooled either before or after it is divided and this step may include some condensation in which case the condensate is separated from the gas. One of the divided gas streams is expanded through a work expansion machine down to the pressure of the fractionation column. Any separated condensate is also expanded to the column pressure. The second divided gas stream is further cooled by heat exchange and then expanded down to an intermediate pressure whereby a portion is condensed. This condensate is separated from the remaining gas and then expanded to the column pressure. The remaining gas is further cooled and expanded and fed to the column as the top feed.

8 Claims, 3 Drawing Figures

HYDROCARBON GAS SEPARATION

BACKGROUND OF THE INVENTION

The present invention relates to an improved cryogenic gas separation process.

Mixtures of gases are frequently separated into the component gases by cryogenic techniques. An example is the separation of ethane (and heavier hydrocarbons) from methane. Recent increases in the market for ethane, propane and heavier hydrocarbons have created the need for processes yielding higher recovery of these products.

Several variations of prior art cryogenic separation processes are described in U.S. Pat. No. 4,278,457 issued July 14, 1981 and the present invention will be compared to the processes disclosed in that U.S. patent.

U.S. Pat. No. 4,278,457 deals primarily with the problem of increasing ethane recovery while at the same time reducing the danger of $CO_2$ icing. This is accomplished by splitting the vapor stream to the demethanizer column into two portions. This was found to reduce the risk of $CO_2$ icing without increasing column overhead temperature so that the ethane recovery was not adversely effected. The vapors can be split either before or after the preliminary cooling stages. The first portion of the vapor is cooled to substantial condensation, expanded to the column operating pressure and supplied as a column feed usually at the top of the column. The second portion of the vapor is expanded through a work expansion machine. This stream is cooled sufficiently prior to expansion so that the column top temperature can be controlled by the column top feed. The column refrigeration is provided by the combined cooling effect of the first and second portions of the split vapor feed. Any condensed liquids that result can be expanded and supplied as a lower mid-column feed.

SUMMARY OF THE INVENTION

In the present invention the feed gas is also split into two portions with one portion being expanded in the normal manner through a work expansion machine and then fed to the column as a mid-point feed. The other portion of the feed gas is cooled and then expanded in a low pressure cold separator to partially condense liquid and separate the liquid from the remaining gas. The liquid from the low pressure cold separator is fed to the column at a mid-point. The vapor from the low pressure cold separator is cooled and expanded and fed to the column as a top feed. The use of this technique of cooling and flashing the one portion of the vapor stream to partially condense and then separating provides a relatively pure methane stream for the top column feed. This superior reflux stream greatly increases the efficiency of the process as compared to prior technology for ethane recovery.

DESCRIPTION OF THE PREFERRED EMBODIMENT

Figure 1:
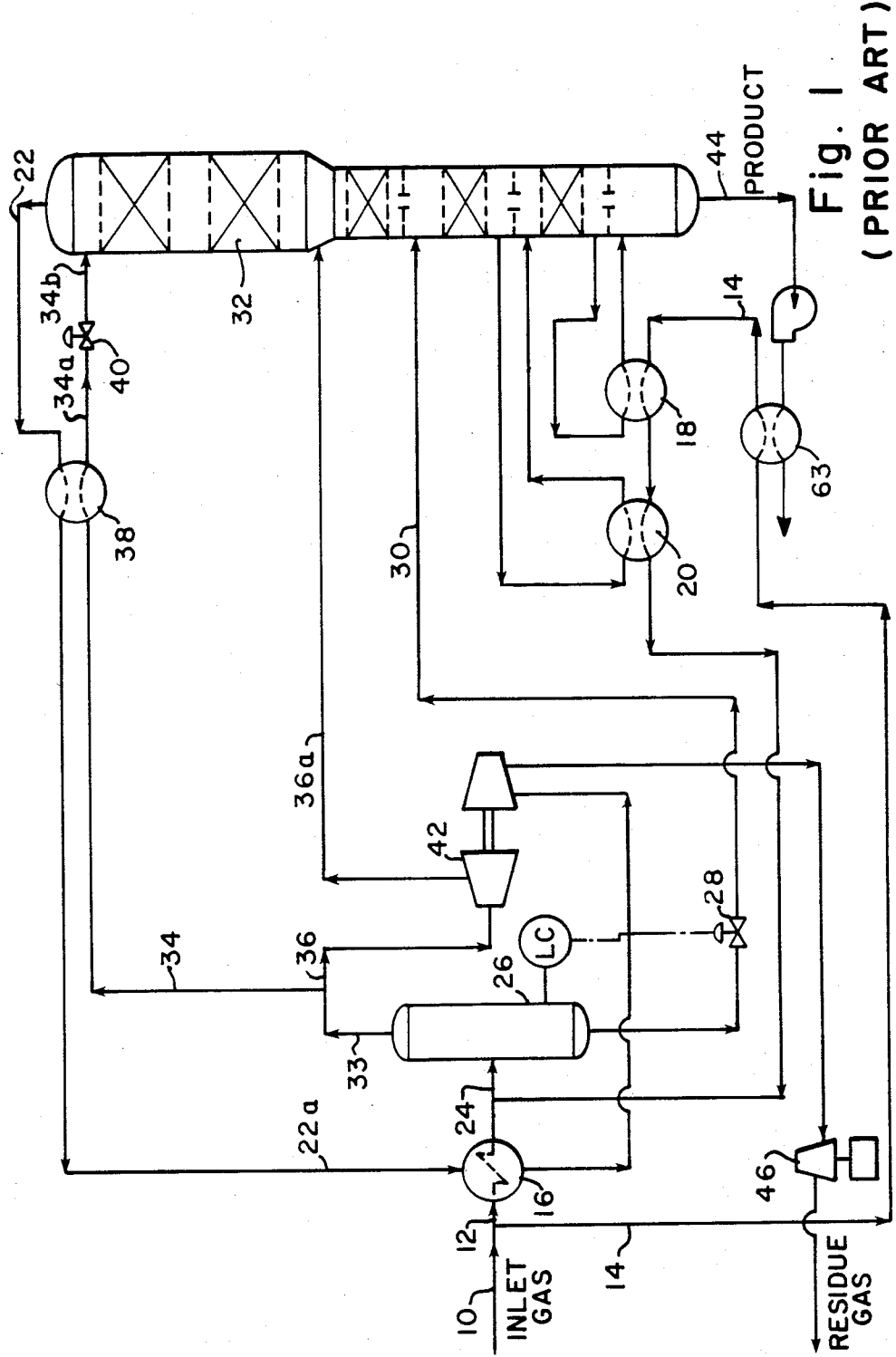
FIG. 1 is a flow diagram of a typical prior art cryogenic natural gas processing plant incorporating a split vapor feed.

Referring first to FIG. 1, inlet gas enters the process at 120° F. and 910 psia as stream 10. This inlet gas stream has been pretreated as necessary to remove any concentration of sulfur compounds and water. This feed stream 10 is split into streams 12 and 14 with the stream 12 being cooled in heat exchanger 16 and stream 14 being cooled in heat exchangers 18 and 20. Heat exchanger 16 is cooled by the residue gas stream 22a. Heat exchangers 18 and 20 are the reboiler and side reboiler for the demethanizer respectively. These feed gas streams 12 and 14 after cooling are then recombined to form a partially condensed, cooled feed gas stream 24 at −30° F. and a pressure of about 910 psia. The vapor and liquid phases in this partially condensed feed gas stream 24 are then separated in the separator 26. The liquid recovered in separator 26 is flash expanded in expansion valve 28 to form the stream 30 at −71° F. and supplied to demethanizer 32 as a lower mid-column feed.

The vapors 33 from separator 26 are divided into two branches 34 and 36. The branch 34 is cooled by residual gas stream 22 in heat exchanger 38 to −120° F. which results in the condensation of substantially all of the stream at 34a. The cooled stream 34a after the heat exchanger 38 is then flash expanded through valve 40 to form the demethanizer top feed stream 34b at a temperature of −164° F.

The branch 36 of the vapor from the cold separator 26 is expanded through the expansion engine 42 to form stream 36a at −125° F. and supplied as the upper mid-column feed to the demethanizer 32. The work from the expansion engine 42 is employed to recompress the residue gas stream 22 after it has passed through the heat exchanger 16. The bottom product from the demethanizer is withdrawn as stream 44. The overhead residual gas stream is recompressed to 900 psia in recompressor 46.

Figure 2:
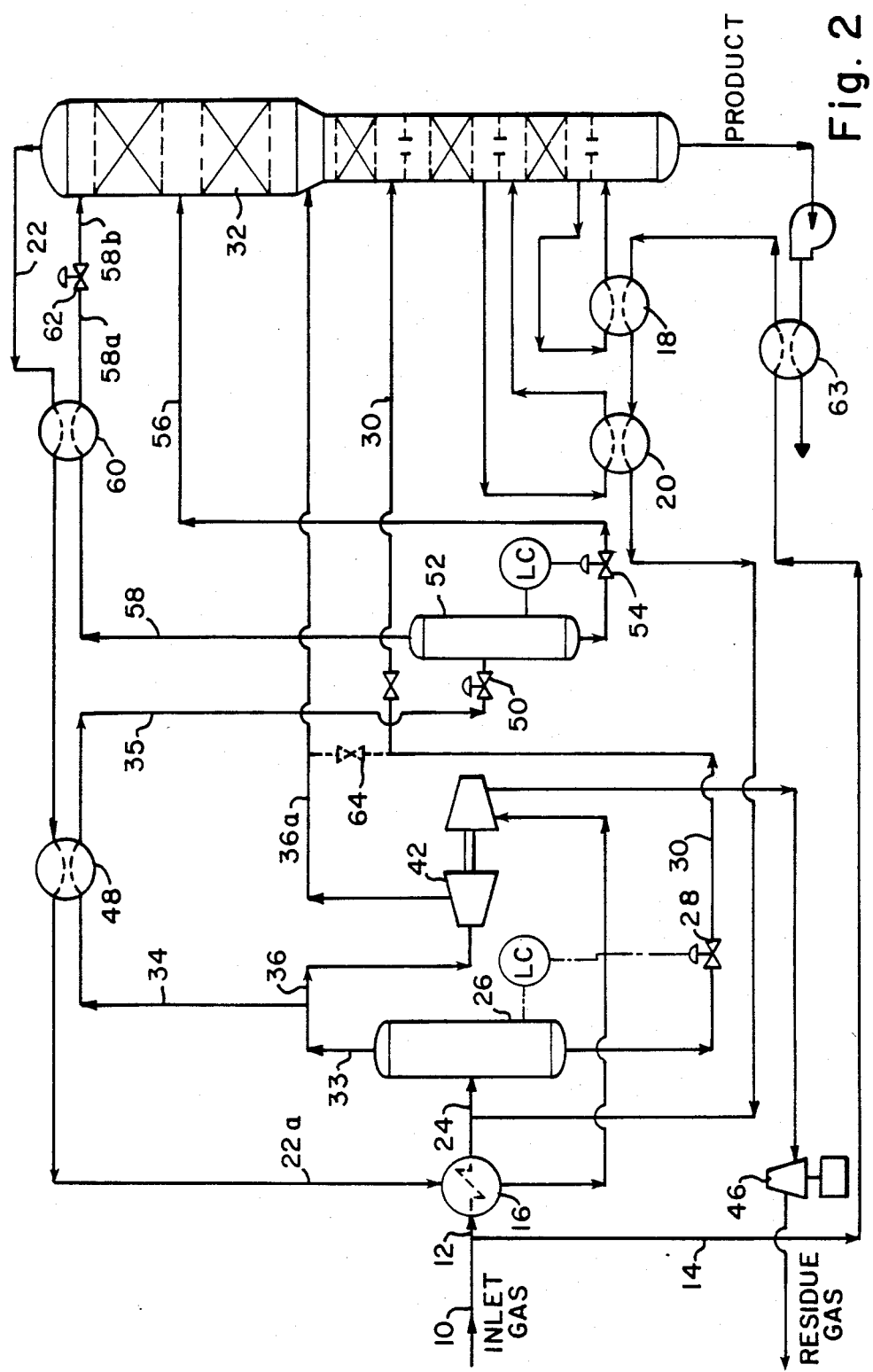
FIG. 2 is a flow diagram of a cryogenic natural gas processing plant in accordance with the present invention.

FIG. 2 which illustrates one embodiment of the present invention will now be referred to and compared to the prior art shown in FIG. 1. Like reference numerals refer to like process steps or equipment or process streams.

In the FIG. 2 embodiment of the present invention, the vapors 33 from the high pressure cold separator 26 are again split into two streams 34 and 36. Stream 36 is expanded in the usual fashion through the expansion engine 42 to form stream 36a which is supplied to the demethanizer 32 as an upper mid-column feed. The liquid from the high pressure cold separator 26 is also treated just as in the prior art and is expanded through valve 28 and then fed as stream 30 to the demethanizer 32 as the lower mid-column feed.

The remaining vapor stream 34 from the high pressure cold separator 26 which has a temperature of about −42° F. is partially condensed in the heat exchanger 48 by heat exchange contact with the residue gas stream 22 from the top of the demethanizer 32. This partially condensed vapor stream 35, which is typically 60 to 70% liquid on a molar basis, is then expanded to an intermediate pressure through the expansion valve 50 resulting in about 30 to 60% liquid on a molar basis. The liquid is separated from the vapor in the low pressure cold separator 52. The liquid from the low pressure cold separator 52 is expanded through the expansion valve 54 to form stream 56 which is supplied to the demethanizer 32 as a lower top-column feed. The vapor from the low pressure cold separator 52 is fed as stream 58 through the heat exchanger 60 in heat exchange contact with the residue gas stream 22 from the top of the demethanizer 32 to form a stream 58a at a temperature of about −130° F. This stream 58a is then expanded through valve 62 forming stream 58b at a temperature of −169° F. which is then supplied as the upper top-column feed to the demethanizer 32. The product from the bottom of the demethanizer 32 is pumped through heat exchanger 63 to provide additional cooling for stream 14. Typical compositions for the feeds to the column for the FIG. 2 embodiment in mole % would be as follows:

TABLE I

| Component | Stream 36 | Stream 58 | Stream 56 |
|---|---|---|---|
| Nitrogen | 1.19 | 1.67 | 0.55 |
| Carbon Dioxide | 0.71 | 0.50 | 1.01 |
| Methane | 91.87 | 96.06 | 86.18 |
| Ethane | 4.56 | 1.62 | 8.53 |
| Propane | 1.18 | 0.13 | 2.60 |
| i-Butane | 0.22 | 0.01 | 0.50 |
| i-Pentane | 0.23 | 0.01 | 0.54 |
| Pentane Plus | 0.04 | — | 0.09 |
| TOTAL | 100.00 | 100.00 | 100.00 |

One variation of the present invention which is shown in FIG. 2 is that the liquid stream 30 which is withdrawn from the bottom of the high pressure cold separator 26 through the expansion valve 28 may be combined with stream 36a through valve 64 (which would otherwise be closed) to form one mid-column feed rather than the two separate upper and lower mid-column feeds.

A stream flow summary comparing the prior art process of FIG. 1 with the processes of FIG. 2 (both the 3 stream feed and the 4 stream feed to the demethanizer) is set forth in Table II which follows. In the table, compositions expressed as flow rates are given in pound moles per hour. The following assumptions and criteria were used in the computer simulation to develop the stream flow summary comparison.

1. The inlet gas contains 19 pound moles per hour of nitrogen.
2. The split between iso and normal butane and hexanes was assumed.
3. The expansion engine efficiency was assumed to be 78%.
4. The expansion engine compressor efficiency was assumed to be 72%.
5. The expander engine bearing loss was assumed to be 2%.
6. The demethanizer was assumed to have 14 theoretical stages.
7. The recompressor efficiency was assumed to be 75%.
8. The physical property data used was SRK K-values and RICE enthalpies.

TABLE II

Figure 3:
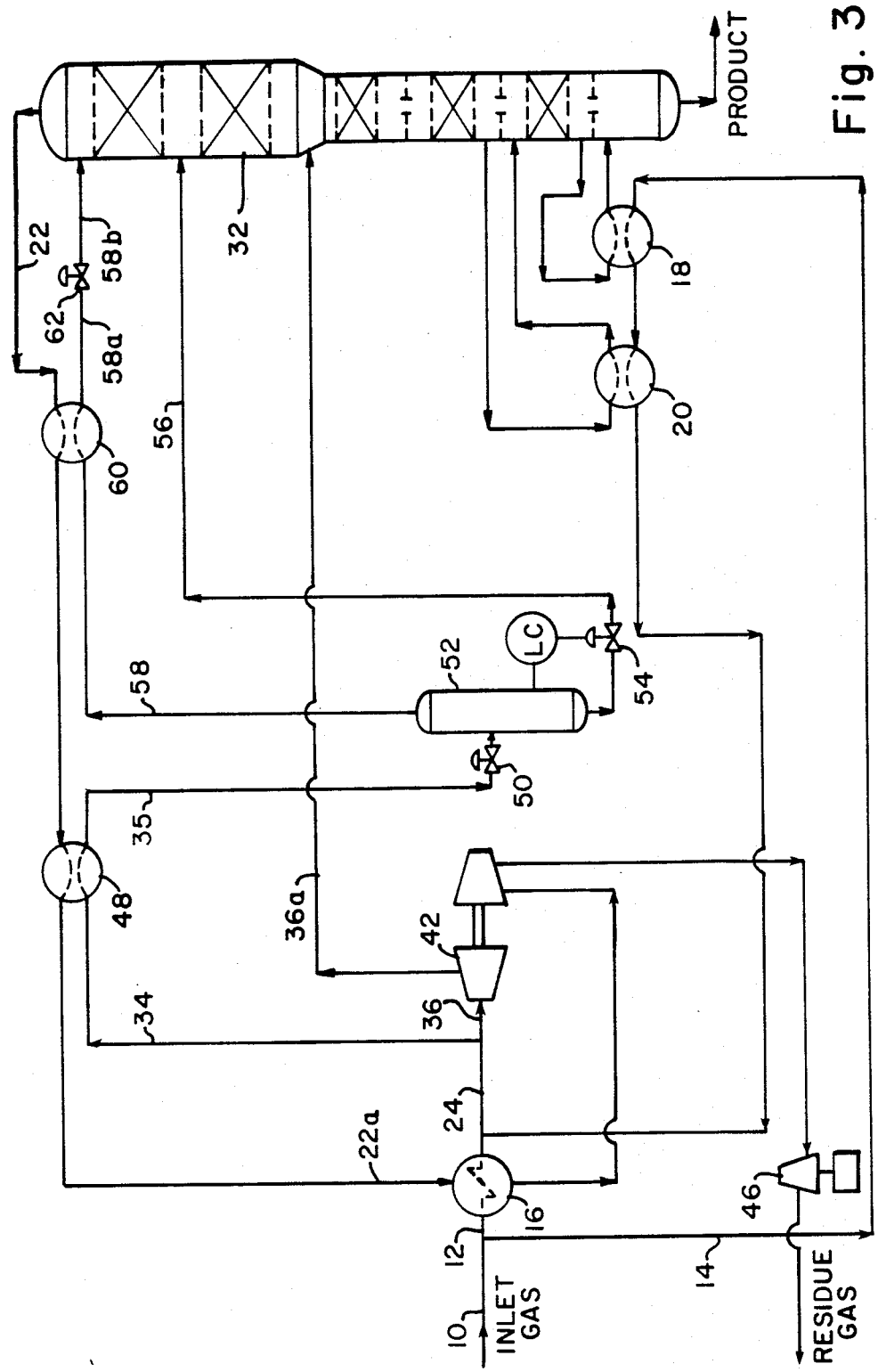
FIG. 3 is a flow diagram of a variation of the present invention.

| | FIG. 1 (Prior Art) | FIG. 2 3 Feeds | FIG. 2 4 Feeds |
|---|---|---|---|
| Inlet Gas Composition, Mol/Hr | | | |
| Nitrogen | 19 | 19 | 19 |
| Carbon Dioxide | 12 | 12 | 12 |
| Methane | 1,447 | 1,447 | 1,447 |
| Ethane | 90 | 90 | 90 |
| Propane | 36 | 36 | 36 |
| i-Butane | 11 | 11 | 11 |
| n-Butane | 15 | 15 | 15 |
| Hexanes | 17 | 17 | 17 |
| TOTAL | 1,647 | 1,647 | 1,647 |
| Bottom Product Composition, Mol/Hr | | | |
| Carbon Dioxide | 2.0 | 2.0 | 2.0 |
| Methane | 2.6 | 2.7 | 3.0 |
| Ethane | 76.5 | 77.3 | 81.5 |
| Propane | 35.8 | 35.9+ | 35.9+ |
| i-Butane | 11.0 | 11.0 | 11.0 |
| n-Butane | 15.0 | 15.0 | 15.0 |
| Hexanes Plus | 17.0 | 17.0 | 17.0 |
| TOTAL | 159.9 | 160.9 | 165.4 |
| Horsepower Required | 1,165 | 1,181 | 1,178 |
| Product Recovery, % | | | |
| Ethane | 85.0 | 85.9 | 90.6 |
| Propane | 99.4 | 99.9+ | 99.9+ |
| Pressures, psia | | | |
| Stream 10 | 910 | 910 | 910 |
| Stream 58 | — | 565 | 565 |
| Stream 22 | 250 | 250 | 250 |
| Temperatures, °F. | | | |
| Stream 10 | 120 | 120 | 120 |
| Stream 34, 36 | −30 | −42 | −42 |
| Stream 34a, 58a | −120 | −130 | −130 |
| Stream 34b, 58b | −164 | −169 | −169 |
| Stream 36a | −124 | −134 | −134 |
| Stream 22 | −156 | −159 | −161 |
| Stream 22a | −85 | −97 | −101 |
| Heat Balance, MMBTU/HR | +0.09 | +0.04 | +0.04 |

It can be seen from Table II that the same inlet gas composition was used for each case, i.e., the prior art system depicted in FIG. 1 and the present invention depicted in FIG. 2 including both the 3 feed and the 4 feed variations. From the bottom product composition it can be seen that the total amount of bottom product is increased slightly in the case of 3 feeds and significantly increased in the case of 4 feeds over the prior art. Also, the total quantity of propane in the bottom product composition is increased slightly while the total quantity of ethane is increased significantly. The data for the percentage of product recovery shows that the amount of the total propane that is recovered in the bottom product is increased slightly while the amount of total ethane that is recovered in the bottom product is increased significantly, from 85.0% in the case of the prior art up to 85.9% in the case of 3 feeds and 90.6% in the case of 4 feeds in the present invention. Also, it can be seen that this increased product recovery is accomplished with very little change in the horsepower requirements.

FIG. 3 illustrates the present invention as applied to a system in which the feed gas is not partially condensed and which does not utilize the high pressure cold separator 26. In this embodiment, the inlet gas 10 is again divided into streams 12 and 14 with the stream 12 being cooled in heat exchanger 16 and the stream 14 being cooled in the heat exchangers 18 and 20. As in the FIG. 2 embodiment, the streams 12 and 14 after cooling are then recombined to form stream 24. This stream 24, which in this case is still all in the vapor phase, is then split into stream 34 and 36 just as was done with the vapor from the high pressure cold separator in the FIG. 2 embodiment. The stream 36 is supplied to the expansion motor 42 and then supplied as stream 36a to the demethanizer 32 as a lower column feed.

The stream 34 is handled just as in FIG. 2 by passing it through the heat exchanger 48 to form the stream 35 which is then passed through the expansion valve 50 into the low pressure separator 52. The liquid from the low pressure separator is passed through the expansion valve 54 to form the steam 56 which is fed to the demethanizer 32 as a mid-column feed. The vapor from the low pressure cold separator 52 is cooled in the heat exchanger 60 and then expanded through the valve 62 to form the stream 58b which is the upper column feed. Typical compositions for the feeds to the column for the FIG. 3 embodiment in mole % would be as follows:

TABLE III

| Component | Stream 36 | Stream 58 | Stream 56 |
|---|---|---|---|
| Nitrogen | 0.59 | 0.85 | 0.34 |
| Carbon Dioxide | 0.59 | 0.40 | 0.76 |
| Methane | 93.82 | 97.44 | 90.66 |
| Ethane | 3.16 | 1.14 | 4.92 |
| Propane | 1.06 | 0.13 | 1.87 |
| i-Butane | 0.39 | 0.02 | 0.72 |
| n-Butane | 0.39 | 0.02 | 0.73 |
| Pentane Plus | — | — | — |
| TOTAL | 100.00 | 100.00 | 100.00 |

A stream flow summary comparing the process of FIG. 3 with similar prior art processes which do not incorporate the present invention such as, for example, the prior art processes depicted in FIGS. 3, 5 and 6 in the previously mentioned U.S. Pat. No. 4,278,457 is set forth in Table IV which follows. The same assumptions and criteria were used for this comparision except that the inlet gas was assumed to contain 38 pound moles per hour of nitrogen. The ranges given in Table IV for the prior art represent the range of values obtained in the computer simulation of the 3 processes depicted in the previously mentioned figures of U.S. Pat. No. 4,278,457.

TABLE IV

| | Prior Art | FIG. 3 |
|---|---|---|
| Inlet Gas Composition, Mol/Hr | | |
| Nitrogen | 38 | 38 |
| Carbon Dioxide | 39 | 39 |
| Methane | 6,181 | 6,181 |
| Ethane | 208 | 208 |
| Propane | 70 | 70 |
| i-Butane | 26 | 26 |
| n-Butane | 26 | 26 |
| TOTAL | 6,588 | 6,588 |
| Bottom Product Composition, Mol/Hr | | |
| Carbon Dioxide | 3.6–6.7 | 13.4 |
| Methane | 5.3–5.4 | 9.8 |
| Ethane | 178.3–181.9 | 196.8 |
| Propane | 68.8–68.9 | 69.8 |
| i-Butane | | 25.9 | 26.0 |
| n-Butane | 25.9 | 26.0 |
| TOTAL | 311.9–332.0 | 341.9 |
| Horsepower Required | 3,090–3,155 | 3,224 |
| Product Recovery, % | | |
| Ethane | 85.7–87.5 | 94.6 |
| Propane | 98.3–98.4 | 99.8 |
| Pressures, psia | | |
| Stream 10 | 910 | 910 |
| Stream 58 | — | 600 |
| Stream 22 | 360 | 360 |
| Heat Balance, MMBTU/HR | +0.09 | +0.49 |

It can be seen from Table IV that the percentage of total propane removed in the bottom product is increased from about 98.4 up to 99.8% while the percentage of total ethane recovered is increased from about 87.5 up to 94.6%. From the bottom product composition it can be seen that the total amount of bottom product is increased slightly and that the total quantity of ethane in the bottom product is increased significantly. Although it is not shown in the Table, the temperature of the residue gas leaving the top of the demethanizer in the prior art is at −145° F. whereas in the present invention shown in FIG. 3 it is at −149° F.

I claim:

1. In a process for the separation of a feed gas containing methane and ethane into a volatile residue gas containing a major portion of said methane and a relatively less volatile fraction containing a major portion of said ethane wherein methane and ethane together comprise a major portion of said feed gas and wherein said feed gas is cooled under relatively high pressure and then expanded to a relatively low pressure whereby it is further cooled and said further cooled feed stream is fractionated at said relatively low pressure in a fractionation column wherein the overhead temperature is maintained at a temperature whereby the major portion of said ethane is recovered in said less volatile fraction at the bottom of said fractionation column; the improvement comprising:

(a) dividing said feed gas into first and second cooled gaseous streams, (b) expanding said first gaseous stream to said relatively low pressure, (c) further cooling said second gaseous stream at said relatively high pressure and then expanding to an intermediate pressure such that a portion of said second gaseous stream is condensed, (d) separating said condensed portion from the remaining gaseous portion of said second gaseous stream, (e) expanding said separated condensed portion of said second gaseous steam to said relatively low pressure, (f) further cooling said separated remaining gaseous portion of said second gaseous stream and then expanding to said relatively low pressure, and (g) feeding said expanded first gaseous stream (b), said expanded condensed portion of said second gaseous stream (e) and said expanded remaining gaseous portion of said second gaseous stream (f) to said fractionation column at first, second and third feed points, respectively, said third feed point being the top column feed and said second and third feed point being at lower column positions.

2. In a process according to claim 1 wherein said second feed point is above said first feed point.

3. In a process according to claim 1 wherein said feed gas is cooled prior to dividing said feed gas into said first and second cooled gaseous streams.

4. In a process according to claim 3 wherein said feed gas is cooled sufficiently to condense a portion thereof and said condensed portion of said feed gas is separated from the remaining gaseous portion of said feed gas prior to dividing said feed gas into said first and second cooled gaseous streams.

5. In a process according to claim 4 wherein said condensed portion of said feed gas is expanded to said relatively low pressure and fed to said fractionation column at a fourth feed point below said first, second and third feed points.

6. In a process according to claim 4 wherein said condensed portion of said feed gas is expanded to said relatively low pressure and combined with said expanded first gaseous stream (b) for feed to said fractionation column.

7. In a process according to claim 1 wherein that portion of said second gaseous stream which is condensed (c) comprises from 30 to 60% liquid on a molar basis.

8. In a process according to claim 1 wherein said first gaseous stream (b) is expanded in a work expansion machine.

* * * * *